United States Patent [19]
Gates et al.

[11] Patent Number: 5,559,107
[45] Date of Patent: Sep. 24, 1996

[54] REGULATION OF IMMUNE RESPONSE

[76] Inventors: Stephen Gates, 8306 Crosspointe Dr., Fairfax Station, Va. 22039; Roger M. Loria, 3219 Brook Rd., Richmond, Va. 23227

[21] Appl. No.: 325,151

[22] Filed: Oct. 20, 1994

[51] Int. Cl.$^6$ ............................................. A61K 31/56
[52] U.S. Cl. ................................... 514/167; 514/182
[58] Field of Search ........................... 514/171, 182, 514/167; 552/637, 638

[56] References Cited

U.S. PATENT DOCUMENTS

| | | | |
|---|---|---|---|
| 4,978,532 | 12/1990 | El-Rashidy | 424/448 |
| 5,077,284 | 12/1991 | Loria et al. | 514/171 |
| 5,206,008 | 4/1993 | Loria | 424/45 |
| 5,277,907 | 1/1994 | Loria | 424/93 V |
| 5,387,583 | 2/1995 | Loria | 514/171 |
| 5,407,684 | 4/1995 | Loria et al. | 424/442 |

OTHER PUBLICATIONS

Chemical Abstracts, vol. 106, No. 19 issued 18 May 1987, Kubodera et al., "9,10–Secoandrostane (vitamin D) compounds", see page 720, column 2, abstract No. 156775z, Jpn Kokai Tokkyo Koho Jp 61,267,551.

Chemical Abstracts, vol. 117, No. 21 issued 01 Dec. 1992, Sicinski, "Photochemical and thermal isomerizations of 19 functionalized previtamin D analogs in the androstane series", see p. 877, column 1, abstract No. 212780p, Acta Chim. Hung., 129(2), 191–200.

Butenandt, et al., Berichte, 71, 1316–22 (1938).
Milas et al., J. Am. Chem. Soc., 68, 738–40 (1946).

*Primary Examiner*—Kevin E. Weddington
*Attorney, Agent, or Firm*—Glenna Hendricks

[57] ABSTRACT

Androsta-5,7-diene-3β,17β-diol, its esters and ethers and related compounds wherein ring opening of the steroid ring system between carbons 9 and 10 has occurred are active as regulators of immune response and cell proliferation and differentiation.

1 Claim, No Drawings

REGULATION OF IMMUNE RESPONSE

FIELD OF THE INVENTION

This invention relates to compounds having activity as regulators of immune response and cell proliferation and differentiation. Compositions of the invention comprise androsta-5,7-diene-3β,17β-diol its esters and ethers and related compounds wherein there has occurred ring opening of the steroid ring system between carbons 9 and 10.

BACKGROUND OF THE INVENTION

Loria has disclosed that dehydroepiandrosterone, androst-5-ene-3β,17β-diol (AED) and androst-5-ene-3β,7β,17β-triol (AET) are effective as enhancers of immune response (U.S. Pat. Nos. 5,077,284 and 5,206,008, incorporated herein by reference in their entirety). AED and AET have been shown to buffer the effects of hydrocortisone by counteracting the suppressive effects of hydrocortisone on lymphocyte proliferation. Furthermore, under infectious disease conditions, both AED and AET positively enhance lymphocyte proliferation and differentiation of cells.

In vertebrates the development of host protection against pathogens requires a selective host immune response that involves the mobilization of the humoral and/or cellular mediated immune responses. Several factors adversely affect the body's protective response capability by causing prolonged immuno-suppression or "down-regulation" of the immune system. It is, in reality, more appropriate to speak of "mal-regulation" or "deregulation" of the immune system than of "down-regulation" since the result is a failure to protect the body from assault or over-reaction to its immune response. Immuno-suppression provides an opportunity for pathogens to grow in the host. It does not matter what causes the primary insult to immunity. The resulting inability to muster the appropriate immune response has the same effect. Among the many different causes of immuno-suppression are viral, bacterial, fungal, yeast and parasitic infections, chemotherapy, irradiation, severe stress, chronic fatigue syndrome, diabetes mellitus, autoimmune diseases, and some forms of steroid therapy.

It has long been known that patients receiving steroid hormones of adrenocortical origin at pharmacologically appropriate doses show increased incidence of infectious disease. A. S. Fauci, *immunolo. rev.* 65, 133–155 (1982); and J. E. Parillo and A. S. Fauci, *Annual Review of Pharmacology and Toxicology* 19, 179–201 (1979). Dehydroepiandrosterone, also known as 3-β-hydroxyandrost-5-en-17-one or dehydroiso-androsterone (referred to hereinafter as DHEA), is a 17-ketosteroid which is quantitatively one of the major adrenocortical steroid hormones found in mammals. M. E. Windholz, *The Merck Index*, Ninth Edition (1976); K. Diem and C. Lentner, *Geigy Scientific Tables* (1975). (Although DHEA appears to serve as an intermediary in gonadal steroid synthesis, the primary physiological function of DHEA has not been fully understood. It has been known, however, that levels of this hormone begin to decline in the second decade of life, reaching 5% of the original level in the elderly.)

The above-referenced U.S. Pat. No. 5,077,284 entitled "Use of Dehydroepiandrosterone to Improve Immune Response" describes the subcutaneous or oral administration of DHEA to improve the host's response to infections. U.S. Pat. No. 4,978,532 describes use of patch technology to deliver DHEA.

DHEA is a precursor in a metabolic pathway which ultimately leads to more powerful agents that increase immune response in mammals. That is, DHEA acts as a biphasic compound: it acts as an immuno-modulator when converted to androstenediol (androst-5-ene-3β,17β-diol, βAED) or androstenetriol (androst-5-ene-3β,7β,17β-triol, βAET). However, in vitro DHEA has certain lymphotoxic and suppressive effects on cell proliferation prior to its conversion to βAED and/or βAET. It is, therefore, postulated that the superior immunity enhancing properties obtained by administration of DHEA result from its conversion to more active metabolites.

Regulation of the immune system using the active agents of the invention would make it possible to more safely use chemotherapeutic agents. It has previously been disclosed in the aforementioned U.S. Pat. No. 5,206,008 that βAED and βAET (asteroid found in the skin, other epithelial tissue and neuronal tissue) enhance immune response and lymphocytic cell proliferation.

Androsta-5,7-diene-3β,17β-diol has been prepared from androst-5-ene-3β,7β,17β-triol by Butenandt et al., *Berichte*, 71, 1316–1322 (1938) at page 1321, which is incorporated herein by reference in its entirety. Androsta-5,7-diene-3β,17β-diol was also prepared from androst-5-ene-3β,17β-diol by Milas et al., *J. Am. Chem. Soc.*, 68, 738–40 (1946). Both Butenandt and Milas prepared the compound for the purpose of investigating whether it would exhibit antirachitic activity, but no activity was found by either investigator. Butenandt also examined the sex hormone properties of androsta-5,7-diene-3β,17β-diol and determined that it was slightly active in the capon comb test for androgenic activity and also slightly active when used in the immature female rat vagina test for estrogenic activity. Both activity levels were about 1/10 the corresponding activities of androst-5-ene-3β,17β-diol (AED), which in turn has been considered to have very weak androgenic and estrogenic properties. Further, Butenandt and Milas neither investigated nor suggested that androsta-5,7-diene-3β,17β-diol might have any practical medicinal applications. In fact, Butenandt concluded that androsta-5,7-diene-3β,17β-diol had no significant physiological activity.

DETAILED DESCRIPTION OF THE INVENTION

It is the purpose of this invention to provide compositions for use as regulators of immune response and of cell proliferation. The compositions include androsta-5,7-diene-3β,17β-diol, its esters and ethers, and 9,10-secoandrosta-5,7,10(19)-triene-3,17β-diol, its esters or ethers. Exposure of a solution of androsta-5,7-diene-3β,17β-diol or its esters or ethers (I) to ultraviolet irradiation (275–300 nm) at about mammalian body temperature (35°–40° C.) causes ring opening between $C_9$ and $C_{10}$ to form 9,10-secoandrosta-5,7,10(19)-triene-3,17β-diol, its esters or ethers (II), as the case may be.

More particularly, androsta-5,7-diene-3β,17β-diol and its derivatives (I) and 9,10-secoandrosta-5,7,10(19)-triene-3β,17β-diol and its derivatives (II) are represented by the formulas below.

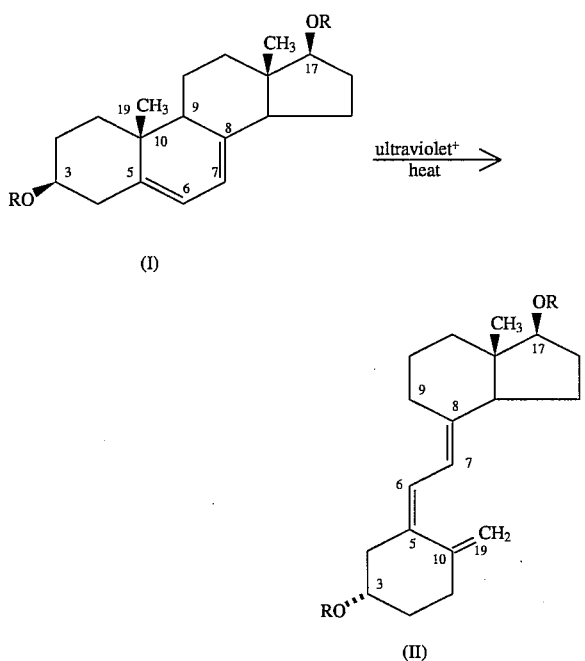

wherein each R individually may be chosen from hydrogen, alkyl having from 1–8 carbons, alkenyl having from 2–8 carbons, phenylalkyl wherein the substituted alkyl has from 1–4 carbons, phenyl, and $COR_1$, wherein each $R_1$ individually may be chosen from alkyl having from 1 to about 8 carbons, alkenyl having from 2 to about 8 carbons, phenylalkyl wherein the alkyl has from 1 to about 4 carbons, and phenyl, wherein any phenyl group may have up to three substituents chosen from among hydroxy, carboxy having from 1 to about 4 carbons, halo, alkoxy having from 1 to about 4 carbons or alkenyl having from 2 to about 4 carbons and wherein any alkyl may be a straight chain, branched chain or wholly or partially cyclized.

The present invention provides compositions useful for enhancing the protective response of the immune system against infections. The medicinal compositions of the invention are also useful for treating other complications often accompanying immune suppression. The enhancement of the protective immune response may also be referred to herein as up-regulation or regulation of immune response. The compositions of the invention alter cytokine production and promote cell differentiation.

The use of androsta-5,7-diene-3β,17β-diol, its metabolites and their protected analogues as taught herein provide high levels of protection to vertebrates, including humans, against morbidity arising from infections or exposure to immune suppressive influences. In clinical medicine, treatment with androsta-5,7-diene-3β,17β-diol, its metabolites and their analogues can lower morbidity in patients exposed to pathogenic organisms. These agents can be effectively used prophylactically in patients known to be particularly susceptible to infection. Patients undergoing surgery or chemotherapy or patients suffering from burns, hypoplastic or aplastic anemias, or diabetes are such susceptible patients who would benefit from prophylactic administration of androsta-5,7-diene-3β,17β-diol, its metabolites and analogues thereof. Also among the causes of immuno-suppression are viral, bacterial, fungal, yeast and parasitic infections, chemotherapy, irradiation, severe stress, chronic fatigue syndrome and some forms of steroid therapy. The compositions of the invention are particularly useful for treating patients suffering from infections which arise when the body's immune response has been compromised by viruses such as human immunodeficiency virus (HIV) and hepatitis.

Active agents of the invention may be formulated using carriers used for steroids. The active agents may be efficiently formulated using lipophilic carriers such as DMSO. For subcutaneous administration to animals used in the examples, the active agents were dissolved 1:1 DMSO/ethanol, then diluted for subcutaneous administration to the animals. When the compositions are administered by mouth, they are added to food to provide a composition containing as little as 0.01% androsta-5,7-diene-3β,17β-diol. For application to the skin, the androsta-5,7-diene-3β,17β-diol may, for example, be dissolved in carrier material containing DMSO and alcohol, then applied to a patch. In such instances, the active agents in solution may be added to another carrier such as glycerol before application of the composition to the support material of the patch. For vaginal or rectal administration, the active agents may be administered by suppository, enema, or by application of creams, etc. Compositions of the invention may be administered by any method that will result in contact of the active agent with tissue of ectodermal origin. Such methods include subcutaneous or intradermal injection or topical application. One means of topical application is the use of skin patches impregnated with the active agent. This means of delivery is advantageous since it is non-invasive and easily administered by relatively unskilled care providers. Compositions of the invention can also be used in veterinary medicine to prevent morbidity that occurs during stress of shipping. Administration of the active agents described herein can be effective as a means to prevent spread of infectious disease and introduction of infectious organisms into the foods for human consumption. The active agents may be administered parenterally by injection, in food or drink, by patches applied to the skin, or by inhalation. A particular health concern is the spread of infection through eggs. Eggs are frequently infected during development in the hen. Compositions containing active agents of the invention may be added to the feed or water to prevent bacterial infection in the eggs.

When patches are used on animals or birds the skin should be exposed directly to the patch. When a patch is used, it may be necessary to pluck or shave the bird or animal to expose the skin.

Other preferred methods of administration include buccal, sublingual, nasal or endotracheal routes. Sprays may be useful for this purpose. For nasal administration, the active agent may be delivered as a powder that is snorted. Inclusion complexes such as cyclodextrin inclusion complexes are appropriate compositions for administration to the oral-pharyngeal and nasal mucosa.

The active agents may also be given with vaccines to enhance immune response and to increase host immune response to infections encountered in the environment before effective desired antibody level is attained. These agents may be administered either in a composition containing the vaccine or may be given in a composition separate from the vaccine.

The active agents of the invention may also be administered to the intestinal mucosa by oral or rectal routes. Suppositories, the intestinal mucosa by oral or rectal routes. Suppositories, solutions for use as retention enemas, and creams or jellies are appropriate carriers for use in rectal administration.

Androsta-5,7-diene-3β,17β-diol, its metabolites and analogues may be applied to the vaginal mucosa using creams, jellies, suppositories, or douching solutions. In order to enhance immune response at the site of exposure to infectious organisms, the compounds may be added to prophylactic vaginal preparations or may be used as lubricants on condoms.

Administration of compositions of the invention when given to patients suffering from encephalitis and meningitis may be administered intrathecally either at the spinal level or into the cisterna magna.

Active agents of the invention may be administered via ocular route using compositions in the form of drops, creams, or gel solutions or suspensions adapted for ocular application.

EXPERIMENTAL

Androsta-5,7,-diene-3β,17β-diol (ADD) was prepared by Steraloids, Inc. using the method of the aforementioned Butenandt reference. The material had the following properties: m.p. 210°–212° C., $[\alpha]20_D$–120° (methanol).

EXAMPLE 1

Use of androsta-5,7-diene-3β,17β-diol results in marked and significant resistance against viral and bacterial infection. The use of androsta-5,7-diene-3β,17β-diol was tested in 3 month old CD1 mice that weighed about 23 g. Control or androsta-5,7-diene-3β,17β-diol in 1:1 DMSO/Ethanol, 0.07 ml, was administered subcutaneously. 2 hours later Simliky Forest Virus (SFV) plus the control or amount of compound indicated in Table I was administered i.p. At the dosages administered, the results (Table I) did not appear to be dose related.

TABLE I

|  | death at 5 PFU/mouse | death at 50 PFU/mouse |
|---|---|---|
| DMSO:Ethanol + SFV (control) | 3/6 | 6/6 |
| androsta-5,7-diene-3β,17β-diol 0.5 mg + SFV | 0/6 | 4/6 |
| androsta-5,7-diene-3β,17β-diol 2.5 mg + SFV | 2/6 | 3/6 |

EXAMPLE 2

The use of androsta-5,7-diene-3β,17β-diol was tested in 28 day old CD1 mice that weighed about 16–17 g. Androsta-5,7-diene-3β,17β-diol in 1:1 DMSO/ethanol and control DMSO/ethanol (0.07 ml) were administered to the respective mice subcutaneously on day 1 followed by administration of West Nile Virus (WNV) in combination with the control or amount of compound indicated in Table II, i.p. on day 2. An additional dosage of 0.5 mg. of androsta-5,7-diene-3β,17β-diol in 1:1 DMSO/ethanol was administered to the test animals on day 3. The results (Table II) did not appear to be dose-related at the dosages administered.

TABLE II

|  | death/sample 5 PFU/mouse | death/sample 50 PFU/mouse | |
|---|---|---|---|
|  |  | Day 7 | Day 10 |
| DMSO:Ethanol + WNV (control) | 3/6 | 5/6 | 6/6 |
| androsta-5,7-diene-3β,17β-diol | 0/6 | 3/6 | 3/6 |

TABLE II-continued

|  | death/sample 5 PFU/mouse | death/sample 50 PFU/mouse | |
|---|---|---|---|
|  |  | Day 7 | Day 10 |
| 0.5 mg + WNV androsta-5,7-diene-3β,17β-diol 2.5 mg + WNV | 2/6 | 3/6 | 3/6 |

(mortality in controls occurred on days 7–9, in treated group on days 8–10)

The carrier used in a given instance will depend on the mode of administration. Since the active agents are steroids or steroid-like, solvents for lipophilic steroids are known in the art and would be used as carriers for these compounds. Examples of such carriers are glycols such as polypropylene glycol, polyethylene glycol and cyclodextrins, especially the intrinsically amorphous cyclodextrins. Other vehicles that should be considered include fatty acid esters of polyoxyethylene sorbitan (Tweens) or sorbitan (Spans) to prepare oil-in-water emulsions.

EXAMPLE 3

Capsules of a formulation of androsta-5,7-diene-3β,17β-diol for oral administration are prepared by containing 1 mg. androsta-5,7-diene-3β,17β-diol, 150 mg. starch, and 5 mg. magnesium stearate. The capsules are administered daily or twice a day to achieve a daily dosage of 2 mg. per day.

EXAMPLE 4

Androsta-5,7-diene-3β,17β-diol is added to the chow of the animals at a rate of 0.04% of the diet.

A preparation for application to the skin or mucosa may be prepared in the following manner:

| Ingredient | % w/w |
|---|---|
| androsta-5,7-diene-3β,17β-diol | 0.1% |
| glyceryl monostearate | 3.0% |
| propylene glycol | 13.0% |
| Petrolatum | 83.9% |

When active agents described herein are administered orally, the active agents may be utilized more efficiently if the active agents are protected from destruction and absorption in the upper gastro-intestinal tract. The active agents are most effective when the period of exposure to the mucosa of the intestinal tract is increased. Hence use of capsules containing the active agents in formulations that effect slow release in the intestine are appropriate for treatment of intestinal disorders such as Crohn's disease and colitis. Use of retention enemas for treatment of inflammation of the large bowel is also appropriate.

EXAMPLE 6

A formulation for administration as a retention enema may be formulated in the following manner:

| Ingredient | w/w % |
|---|---|
| androsta-5,7-diene-3β,17β-diol | 1% |
| glycerol | 99% |

When the active agent is administered to the mucosa of the oral cavity, it may be administered as a buccal tablet or spray for use in the oral-pharyngeal cavity and the nasal cavities.

EXAMPLE 7

A formulation for administration of 9,10-secoandrosta-5, 7,10(19)-triene-3β,17β-diol is prepared for oral dosage form in a soft gelatin capsule:

| Ingredient | Amount mg/capsule |
| --- | --- |
| 9,10-secoandrosta-5,7,10(19)-triene-3β,17β-diol | 0.0001–0.010 |
| butylated hydroxytoluene (BHT) | 0.015 |
| Butylated hydroxyanisole (BHA) | 0.015 |
| Fractionated coconut oil | 160.0 |

1. Mix BHT and BHA in coconut oil and warm to about 50° C.
2. Add 9,10-secoandrosta-5,7,10(19)-triene-3β,17β-diol to coconut oil mixture under nitrogen.
3. Fill soft capsules with the 9,10-secoandrosta-5,7,10(19)-triene-3β,17β-diol/oil mixture.

EXAMPLE 8

Solution of 9,10-secoandrosta-5,7,10(19)-triene-3β,17β-diol for intravenous administration is formulated as a sterile, isotonic aqueous solution. 1 ml contains:

| | |
| --- | --- |
| 9,10-secoandrosta-5,7,10(19)-triene-3β,17β-diol | 1–2 μg |
| Polysorbate 20 | 4 mg |
| sodium chloride | 1.5 mg |

The compositions could also be administered to the bronchial tree via inhalation. This means of administration would be particularly useful in treating patients with lung infections or in treating other lung conditions such as black lung disease or emphysema that often are complicated by opportunistic infections. The compositions could be given by aerosol into the trachea or administered in mist along with other agents used in respiration therapy.

The administration of the active agents to the skin can be accomplished using patches wherein a support is impregnated with the active agent or using implants that provide slow release of the active agents.

Patches for the administration of androsta-5,7-diene-3β,17β-diol and other active agents described herein can be formulated as adhesive patches containing the drug. For example, the patch may be a discoid in which a pressure-sensitive silicone adhesive matrix containing the active agent may be covered with a non-permeable backing. The discoid may either contain the active agent in the adhesive or may have attached thereto a support made of material such as polyurethane foam or gauze that will hold the active agent. Before use, the material containing the active agent would be covered to protect the patch.

The administration of the active agents to the skin can be accomplished using patches wherein a support is impregnated with the active agent or using implants that provide slow release of the active agents.

Patches for the administration of androsta-5,7-diene-3β,17β-diol and other active agents described herein can be formulated as adhesive patches containing the drug. For example, the patch may be a discoid in which a pressure-sensitive silicone adhesive matrix containing the active agent may be covered with a non-permeable backing. The discoid may either contain the active agent in the adhesive or may have attached thereto a support made of material such as polyurethane foam or gauze that will hold the active agent. Before use, the material containing the active agent would be covered to protect the patch.

EXAMPLE 9

A patch composed of trilaminate of an adhesive matrix sandwiched between a non-permeable backing and a protective covering layer is prepared in the following manner:

To a pressure-sensitive silicone adhesive composition BIOPSA™ Q7-2920 (Dow Corning Corp., Midland, Mich., U.S.A.) in cyclohexane (50% w/v) is added sufficient βAED to provide a 0.5% βAED composition. The adhesive is applied to a polyester film to provide in successive layers to provide about 0.5 mg of active agent per $cm^2$. The film containing the adhesive is then made into patches of 10 $cm^2$. Patches would be covered with a protective layer to be removed before application of the patch. Patches may be prepared containing permeation enhancers such as cyclodextrin, butylated hydroxyanisole, or butylated hydroxytoluene. However, it should be remembered that the active agents of this invention are effective on application to the epidermal tissue. When the patches are to be applied to thin or abraded skin, there is little need to add a permeation enhancer.

Compositions of the invention can be administered as a prophylactic during radiation therapy or chemotherapy or after exposure to irradiation whether the exposure occurs as a result of environmental accident or therapy. Other instances when use of these immune up-regulators would be appropriate is in treatment of burns, hypoplastic and aplastic anemias, diabetes, and in the elderly during epidemics. Their use is also beneficial in preventing or mitigating effects of exposure to dangerous infectious organisms, as was demonstrated by the data related to cardiopathies and pancreopathies. Such use is particularly indicated in populations exposed to organisms that target the immune system, such as HIV infections. In certain instances the compositions taught herein can also be used as immune modulators in the production of blocking antibodies to counteract hypersensitivity reactions.

As indicated previously, patients scheduled to undergo bowel surgery or other "dirty" surgical procedures could receive a dose of the active agents as taught herein prophylactically. Use of the compositions as taught herein before invasive dental procedures or oral surgery should be considered.

The active agents described herein may be used as adjuncts in vaccination to increase response to an immunogen, to increase response to the vaccine, and to protect against disease before the body has responded with increase in specific antibodies. Such use is particularly appropriate in instances where inhibition of immune response can be a complicating factor as is the case in patients suffering from, for example, malignancies, AIDS, or environmental factors such as exposure to pesticides. It is, of course, understood that use as adjunct to vaccination would be appropriate in vertebrates other than man, including vaccination of pets, dairy animals, meat-producing animals, fish, and chickens. Chickens are particularly prone to develop infectious diseases when living in confined conditions. Coccidiosis, Salmonella infections, viral infections, including those giving rise to malignancies such as leukemia and sarcoma (caused by a retrovirus) are particularly common among chickens grown under modern commercial conditions.

In vitro, these compounds can be used in a commercial setting to induce cell differentiation. The use of the active agents would increase yield of products of such proliferation in tissue culture. In the clinical setting, the compositions may be administered to effectively enhance patients' ability to combat infections.

The active agents disclosed herein regulate cytokine production, thus effecting cell differentiation. Compositions of the invention also encourage cell differentiation, which would benefit patients suffering from malignancies such as melanoma and leukemia.

The compositions of the invention may also be used prophylactically to protect animals from the consequences of infection by pathogenic organisms. It is known that under the stress of shipment to market animals often become susceptible to infections that are not ordinarily serious, but that can cause the animals to loss much weight en route to the packing house. Such loss may be avoided by administration of androsta-5,7-diene-3β,17β-diol or 9,10-secoandrosta-5,7,10(19)-triene-3β,17β-diol or their esters or ethers as disclosed herein. The active agents can be given by patch, injection, or in feed. Because the active agents are most effective when the period of exposure to the tissue of ectodermal origin is extended, when the active agents are administered through the GI tract, compositions should be modified to extend the period of exposure of the active agent to the intestinal mucosa and to protect the agents from destruction in the upper GI tract. Hence, use of capsules that effect slow release in the intestine is appropriate. The capsules may be placed in baits for administration to animals. To treat infections of the large bowel, the active agents may be given by retention enema.

The active agents may be administered to the mucosa of oral, pharyngeal, and nasal cavity by tablet, a lozenge, by administration as a spray for use in the oral-pharyngeal cavity, or as a nasal spray.

Administration to the skin may be accomplished using patches wherein a support to be applied to the skin is impregnated with the active agent. If the host is a mammal or bird, it may be necessary to shave or pluck the region to which the patch is applied.

A preferred method of administration of the diene or triene, or their ethers or esters, is by subcutaneous injection as a depo. The method is particularly appropriate for administration of the active agents to mammals, since subcutaneous injection is easily performed and the effect is relatively long lasting.

The dosages used will depend on the size and condition of the host. Test data indicated in this application was obtained in small animals. In larger adult mammals daily dosage of 0.1 to 30 mg/da. of androsta-5,7-diene-3β,17β-diol is a preferred dosage. For compounds of the irradiated species having the steroid ring open at between the 9 and 10 carbons, the preferred dosage is usually in the range of 0.001 to 20 mg/da, with 0.001 to 1 mg/da. being the more preferred dosage. However, the dosage will vary depending on the route of administration. Subcutaneous, inhalation and intrathecal administration are methods that would require lower dosages of the active agents.

It is, of course, understood that analogues of androsta-5, 7-diene-3β,17β-diol or 9,10-secoandrosta-5,7,10(19)-triene-3β,17β-diol having protective groups can be administered to the host as a means of delivering them to target tissues. Acylation is a preferred method of protecting the compounds. Acylated compounds wherein $R_1$ is $COR_2$ are also appropriate compounds for use as starting material from which to make analogues.

The active agents can be given in conjunction with other active agents which may be given simultaneously or may be incorporated in compositions containing the active agents described herein and can be given with anti-infective agents such as antibiotics, antiviral agents, antifungals, antiparasitic agent to potentiate the activity of these drugs by up-regulating protective immune response. Antiviral agents include, for example, dideoxyinosine, AZT, acyclovir, etc.

Finally, medicinal compositions of the invention are particularly valuable for use in combating infections in patients whose immune defenses have been damaged by immunosuppressive therapy. One of the major complications in patients with tissue transplants is the opportunistic infection with viruses that ordinarily do not cause serious disease symptoms. Use of the compositions of the invention, which result in rapid protective regulation of the immune response, allows the medical team to place the patient on "see-saw" therapy to avoid transplant rejection while regulating the immune response to avoid overwhelming infection.

We claim:

1. A method of enhancing immune response in a mammal by the administration of an immune enhancing-effective amount of a composition containing as an active agent at least one compound of the formula:

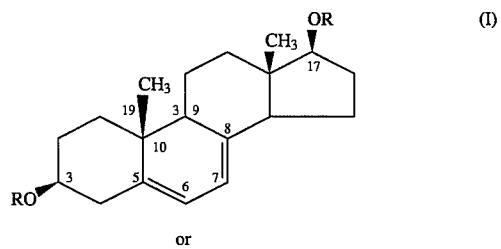

(I)

or

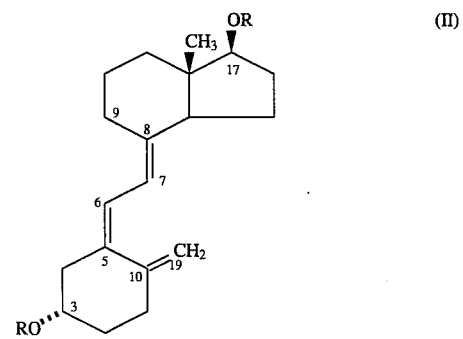

(II)

wherein each R individually is chosen from hydrogen, alkyl having from 1–8 carbons, alkenyl having from 2–8 carbons, phenylalkyl wherein the alkyl has from 1–4 carbons, phenyl, and $COR_1$, wherein each $R_1$ individually is chosen from alkyl having from 1 to about 8 carbons, alkenyl having from 2 to about 8 carbons, phenylalkyl wherein the alkyl has from 1 to about 4 carbons, and phenyl, wherein any phenyl group may have up to three substituents chosen from among hydroxy, carboxy having from 1 to about 4 carbons, halo, alkoxy having from 1 to about 4 carbons or alkenyl having from 2 to about 4 carbons and wherein any alkyl is a straight chain, branched chain or wholly or partially cyclized.

* * * * *